US009232962B2

(12) United States Patent
Surti et al.

(10) Patent No.: US 9,232,962 B2
(45) Date of Patent: Jan. 12, 2016

(54) APPARATUS FOR SINGLE PORT ACCESS (75) Inventors: Vihar C. Surti, Winston-Salem, NC (US); Richard W. Ducharme, Winston-Salem, NC (US); Tyler Evans McLawhorn, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 471 days.

(21) Appl. No.: 12/896,373

(22) Filed: Oct. 1, 2010

(65) Prior Publication Data
US 2011/0082345 A1 Apr. 7, 2011

Related U.S. Application Data (60) Provisional application No. 61/248,204, filed on Oct. 2, 2009.

(51) Int. Cl.
A61B 1/32 (2006.01)
A61B 17/34 (2006.01)
A61B 17/02 (2006.01)

(52) U.S. Cl.
CPC ......... *A61B 17/3423* (2013.01); *A61B 17/0293* (2013.01); *A61B 2017/3445* (2013.01)

(58) Field of Classification Search
CPC ............... A61B 17/02; A61B 17/0206; A61B 17/0212; A61B 17/0128; A61B 17/0281; A61B 17/3403; A61B 17/3405; A61B 17/3407; A61B 17/3421; A61B 2017/3423; A61B 2017/3445; A61B 2017/347; A61B 17/0293
USPC ................. 600/184–246, 104, 114, 121, 381; 606/99–100; 356/241.1–241.6
See application file for complete search history.

(56) References Cited

U.S. PATENT DOCUMENTS

| | | | | |
|---|---|---|---|---|
| 3,677,262 A | * | 7/1972 | Zukowski | 600/120 |
| 3,858,577 A | * | 1/1975 | Bass et al. | 600/108 |
| 4,593,682 A | * | 6/1986 | Heckele | 600/139 |
| 4,640,124 A | * | 2/1987 | Diener et al. | 73/114.01 |
| 4,640,273 A | * | 2/1987 | Greene et al. | 128/861 |
| 5,133,336 A | | 7/1992 | Savitt et al. | |
| 5,469,853 A | * | 11/1995 | Law et al. | 600/463 |
| 5,522,788 A | | 6/1996 | Kuzmak | |

(Continued)

FOREIGN PATENT DOCUMENTS

| | | |
|---|---|---|
| GB | 2031281 | 4/1980 |
| GB | 2052996 | 2/1981 |

OTHER PUBLICATIONS

International Search Report/Written Opinion for PCT/US2010/051111 (Jan. 1, 2011).

(Continued)

*Primary Examiner* — Mary Hoffman
(74) *Attorney, Agent, or Firm* — Brinks Gilson & Lione (57) ABSTRACT

Medical devices, systems and methods are disclosed that serve to guide one or more medical devices through a port formed in bodily tissue to access a bodily cavity. One embodiment of the medical device includes a connection member, a rail, and a carrier. The connection member is structured for attachment to the port. The rail is attached to the connection member, and has a first portion extending distally through the port opening, and a second portion extending at an angle relative to the first portion. The carrier is structured to selectively connect to the first portion of the rail, and is slidable along the first and second portions of the rail.

24 Claims, 7 Drawing Sheets

(56) References Cited

U.S. PATENT DOCUMENTS

| | | | |
|---|---|---|---|
| 5,547,458 A * | 8/1996 | Ortiz et al. | 600/204 |
| 5,569,165 A * | 10/1996 | Chin et al. | 600/204 |
| 5,571,215 A * | 11/1996 | Sterman et al. | 600/101 |
| 5,716,327 A * | 2/1998 | Warner et al. | 600/204 |
| 5,749,889 A | 5/1998 | Bacich et al. | 606/198 |
| 5,913,818 A * | 6/1999 | Co et al. | 600/204 |
| 6,071,233 A * | 6/2000 | Ishikawa et al. | 600/104 |
| 6,235,028 B1 * | 5/2001 | Brumfield et al. | 606/53 |
| 6,416,469 B1 | 7/2002 | Phung et al. | |
| 6,539,942 B2 | 4/2003 | Schwartz et al. | |
| 6,878,106 B1 * | 4/2005 | Herrmann | 600/104 |
| 7,553,227 B2 | 6/2009 | Landuyt | |
| 7,575,548 B2 | 8/2009 | Takemoto et al. | |
| 7,658,738 B2 | 2/2010 | Nobis et al. | |
| 7,717,847 B2 | 5/2010 | Smith | |
| 7,749,198 B2 | 7/2010 | Smith | |
| 7,753,901 B2 | 7/2010 | Piskun et al. | |
| 7,762,990 B2 | 7/2010 | Judson et al. | |
| 7,766,810 B2 | 8/2010 | Ohdaira | |
| 7,798,998 B2 | 9/2010 | Thompson et al. | |
| 7,806,870 B2 | 10/2010 | Mastri et al. | |
| 7,815,565 B2 | 10/2010 | Stefanchik et al. | |
| 8,100,951 B2 * | 1/2012 | Justis et al. | 606/279 |
| 2002/0161368 A1 * | 10/2002 | Foley et al. | 606/61 |
| 2004/0230095 A1 * | 11/2004 | Stefanchik et al. | 600/104 |
| 2004/0230096 A1 * | 11/2004 | Stefanchik et al. | 600/106 |
| 2004/0230097 A1 * | 11/2004 | Stefanchik et al. | 600/127 |
| 2005/0096508 A1 | 5/2005 | Valentini et al. | |
| 2006/0258907 A1 * | 11/2006 | Stefanchik et al. | 600/121 |
| 2007/0055108 A1 | 3/2007 | Taylor et al. | |
| 2007/0173687 A1 * | 7/2007 | Shima et al. | 600/106 |
| 2008/0132758 A1 * | 6/2008 | Stefanchik et al. | 600/104 |
| 2008/0146881 A1 * | 6/2008 | Alimi et al. | 600/204 |
| 2008/0287743 A1 | 11/2008 | Smith et al. | |
| 2008/0300547 A1 | 12/2008 | Bakos | |
| 2008/0319258 A1 | 12/2008 | Thompson | |
| 2009/0054728 A1 | 2/2009 | Trusty | |
| 2009/0143643 A1 | 6/2009 | Weitzner et al. | |
| 2009/0149714 A1 | 6/2009 | Bonadio | |
| 2009/0192465 A1 | 7/2009 | Smith | |
| 2009/0259172 A1 | 10/2009 | Yamaoka et al. | |
| 2009/0275798 A1 | 11/2009 | Naito | |
| 2009/0275967 A1 | 11/2009 | Stokes et al. | |
| 2009/0276055 A1 | 11/2009 | Harris et al. | |
| 2010/0010298 A1 | 1/2010 | Bakos et al. | |
| 2010/0010299 A1 | 1/2010 | Bakos et al. | |
| 2010/0036200 A1 | 2/2010 | Okada | |
| 2010/0042078 A1 | 2/2010 | Okada | |
| 2010/0049162 A1 | 2/2010 | Hameed | |
| 2010/0063358 A1 | 3/2010 | Kessler | |
| 2010/0063359 A1 | 3/2010 | Okoniewski | |
| 2010/0081863 A1 | 4/2010 | Hess et al. | |
| 2010/0081864 A1 | 4/2010 | Hess et al. | |
| 2010/0081871 A1 | 4/2010 | Widenhouse et al. | |
| 2010/0081877 A1 | 4/2010 | Vakharia | |
| 2010/0081880 A1 | 4/2010 | Widenhouse et al. | |
| 2010/0081881 A1 | 4/2010 | Murray et al. | |
| 2010/0081882 A1 | 4/2010 | Hess et al. | |
| 2010/0081883 A1 | 4/2010 | Murray et al. | |
| 2010/0081995 A1 | 4/2010 | Widenhouse et al. | |
| 2010/0094284 A1 | 4/2010 | Mikkaichi et al. | |
| 2010/0114033 A1 | 5/2010 | Fischvogt | |
| 2010/0130817 A1 | 5/2010 | Conlon | |
| 2010/0152539 A1 | 6/2010 | Ghabrial et al. | |
| 2010/0160729 A1 | 6/2010 | Smith et al. | |
| 2010/0160735 A1 | 6/2010 | Bakos | |
| 2010/0168519 A1 | 7/2010 | Matsuo | |
| 2010/0168522 A1 | 7/2010 | Wenchell et al. | |
| 2010/0210912 A1 | 8/2010 | Bettuchi | |
| 2010/0211012 A1 | 8/2010 | Hathaway et al. | |
| 2010/0211084 A1 | 8/2010 | Fowler | |
| 2010/0222643 A1 | 9/2010 | Piskun et al. | |
| 2010/0222747 A1 | 9/2010 | Wenchell et al. | |
| 2010/0228090 A1 | 9/2010 | Weisenburgh, II et al. | |
| 2010/0228091 A1 | 9/2010 | Widenhouse et al. | |
| 2010/0228092 A1 | 9/2010 | Ortiz et al. | |
| 2010/0228094 A1 | 9/2010 | Ortiz et al. | |
| 2010/0228096 A1 | 9/2010 | Weisenburgh, II et al. | |
| 2010/0228198 A1 | 9/2010 | Widenhouse et al. | |
| 2010/0234688 A1 | 9/2010 | Carter | |
| 2010/0234806 A1 | 9/2010 | Bettuchi et al. | |
| 2010/0240960 A1 | 9/2010 | Richard | |
| 2010/0241078 A1 | 9/2010 | Barnes | |
| 2010/0249498 A1 | 9/2010 | Wingardner et al. | |
| 2010/0249515 A1 | 9/2010 | Hudon et al. | |
| 2010/0249525 A1 | 9/2010 | Shelton, IV et al. | |
| 2010/0249708 A1 | 9/2010 | Bettuchi et al. | |
| 2010/0249709 A1 | 9/2010 | Fischvogt | |
| 2010/0249711 A1 | 9/2010 | Fischvogt | |
| 2010/0249810 A1 | 9/2010 | Taylor | |
| 2010/0256447 A1 | 10/2010 | Dubi et al. | |
| 2010/0256453 A1 | 10/2010 | Hammond et al. | |
| 2010/0256566 A1 | 10/2010 | Smith | |
| 2010/0256567 A1 | 10/2010 | Smith | |
| 2010/0256636 A1 | 10/2010 | Fernandez et al. | |
| 2010/0261962 A1 | 10/2010 | Friedberg | |
| 2010/0261969 A1 | 10/2010 | Fischvogt et al. | |
| 2010/0261974 A1 | 10/2010 | Shelton, IV et al. | |
| 2010/0261975 A1 | 10/2010 | Huey et al. | |
| 2010/0261976 A1 | 10/2010 | Horton | |
| 2010/0262080 A1 | 10/2010 | Shelton, IV et al. | |
| 2010/0268162 A1 | 10/2010 | Shelton, IV et al. | |
| 2010/0274093 A1 | 10/2010 | Shelton, IV | |
| 2010/0280327 A1 | 11/2010 | Nobis et al. | |
| 2010/0286478 A1 | 11/2010 | Ewers et al. | |
| 2010/0286483 A1 | 11/2010 | Bettuchi et al. | |
| 2010/0286484 A1 | 11/2010 | Stellon et al. | |
| 2010/0286706 A1 | 11/2010 | Judson et al. | |
| 2010/0298646 A1 | 11/2010 | Stellon et al. | |
| 2010/0298775 A1 | 11/2010 | Berry et al. | |
| 2010/0312060 A1 | 12/2010 | Widenhouse et al. | |
| 2010/0312061 A1 | 12/2010 | Hess et al. | |
| 2010/0312063 A1 | 12/2010 | Hess et al. | |
| 2010/0312065 A1 | 12/2010 | Shelton, IV et al. | |
| 2011/0021877 A1 | 1/2011 | Fortier et al. | |
| 2011/0028793 A1 | 2/2011 | Martin et al. | |
| 2011/0028794 A1 | 2/2011 | Widenhouse et al. | |
| 2011/0028795 A1 | 2/2011 | Hotter | |
| 2011/0028891 A1 | 2/2011 | Okoniewski | |
| 2011/0034778 A1 | 2/2011 | Kleyman | |
| 2011/0034935 A1 | 2/2011 | Kleyman | |
| 2011/0034947 A1 | 2/2011 | Kleyman | |

OTHER PUBLICATIONS

Office Action dated Jan. 13, 2015 in related application.
Office Action dated Jun. 3, 2015 in related application.

* cited by examiner

APPARATUS FOR SINGLE PORT ACCESS

CROSS-REFERENCE TO RELATED APPLICATIONS

This invention claims the benefit of U.S. Provisional Application Ser. No. 61/248,204 filed on Oct. 2, 2009, entitled "APPARATUS FOR SINGLE PORT ACCESS," the entire contents of which are incorporated herein by reference.

FIELD OF THE INVENTION

The present invention relates generally to medical devices and systems for use with laparoscopic procedures, and more particularly to apparatus for guiding medical instruments during such procedures.

BACKGROUND OF THE INVENTION

Traditional laparoscopic procedures involve the formation of puncture sites through the skin and related tissue layers to provide access to an internal structure within a bodily cavity. Upon formation of a puncture site, the natural elasticity of the tissue tends to close the opening, and thus a port is utilized to hold the site open. For example, a trocar port is device having a tubular configuration defining a port opening and having a configuration that engages the tissue to hold the site open.

Multiple puncture sites, for example three or more, are provided in the desired area so that multiple instruments may be used for the particular laparoscopic procedure, as well as to allow for triangulation of the target structure. For example, a laparoscope or other visualization system may utilize one port, while a grasper or other tissue manipulator is used with the second port in conjunction with a cutting or suturing device utilized through the third port. While laparoscopic procedures are less invasive when compared to traditional open surgery, these procedures still leave multiple scars.

BRIEF SUMMARY OF THE INVENTION

Embodiments of a medical device for accessing a bodily cavity through a port are provided which enable multiple medical devices to be used through a single port. Generally, the medical devices and systems serve to guide one or more medical devices through the port and within the bodily cavity. One embodiment of a medical device, constructed in accordance with the teachings of the present invention, generally includes a connection member, a rail, and a carrier. The connection member is structured for attachment to the port. The rail is attached to the connection member, and has a first portion extending distally through the port opening, and a second portion extending at an angle relative to the first portion. The carrier is structured to selectively connect to the first portion of the rail, and is slidable along the first and second portions of the rail.

According to more detailed aspects, the rail is structured such that the carrier can slide distally along the rail from the first portion to the second portion. Preferably, the carrier and second portion of the rail are structured such that the carrier cannot be disconnected from the second portion of the rail. The carrier may include an open-sided channel sized to slidably receive the rail. The carrier includes a linking member, and the rail includes an open sided-channel sized to slidably receive the linking member of the carrier. In one embodiment, the rail is formed of a bar having a width, and the first portion has a reduced width section structured to permit the carrier to selectively connect to the rail. The second rail portion is preferably longer than the first portion, and may be straight or curved, and most preferably extends perpendicularly to the first rail portion.

One embodiment of a medical system for accessing a bodily cavity comprises a port, a connection member, a rail, a carrier a medical instrument, and an elongate pusher. The port defines a port opening and is structured for attachment to a bodily wall proximate the bodily cavity. The connection member is structured for attachment to the port. The rail is attached to the connection member and structured to extend through the port opening and into the bodily cavity. The carrier is structured to selectively connect to the rail, and is slidable along the rail for access to the bodily cavity. The carrier also includes an instrument connector. The medical instrument is connected to the instrument connector of the carrier. The elongate pusher member has a distal end connected to the carrier. According to more detailed aspects, the pusher member includes a control wire connected to one of the instrument connector and the medical instrument. The connection member preferably includes a hook-shaped body structured to extend around a proximal rim of the port, and also preferably includes a latch structured to selectively fix the position of the connection member on the port.

One embodiment of a method of accessing a bodily cavity is also provided in accordance with the teachings of the present invention. The method includes providing a medical system such as those described above. The port is attached to a bodily wall proximate the bodily cavity. The rail is passed distally through the port opening and into the bodily cavity. The connection member is attached to the port, and the carrier is attached to the rail. The medical instrument and carrier are slid along the rail and into the bodily cavity.

DETAILED DESCRIPTION OF THE INVENTION

The terms "proximal" and "distal" as used herein are intended to have a reference point relative to the user. Specifically, throughout the specification, the terms "distal" and "distally" shall denote a position, direction, or orientation that is generally away from the user, and the terms "proximal" and "proximally" shall denote a position, direction, or orientation that is generally towards the user.

Figure 1:
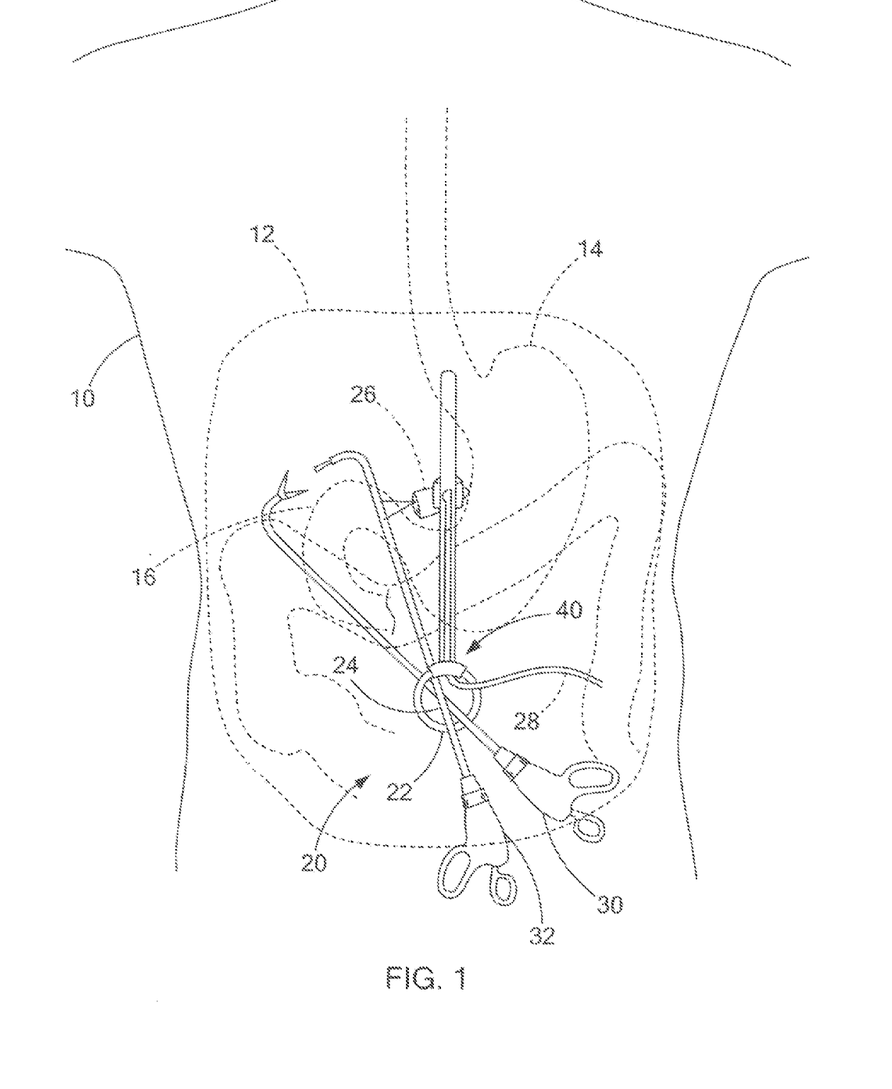
FIG. 1 is schematic plan view depicting one embodiment of the medical system and medical device constructed in accordance with the teachings of the present invention.
Figure 2:
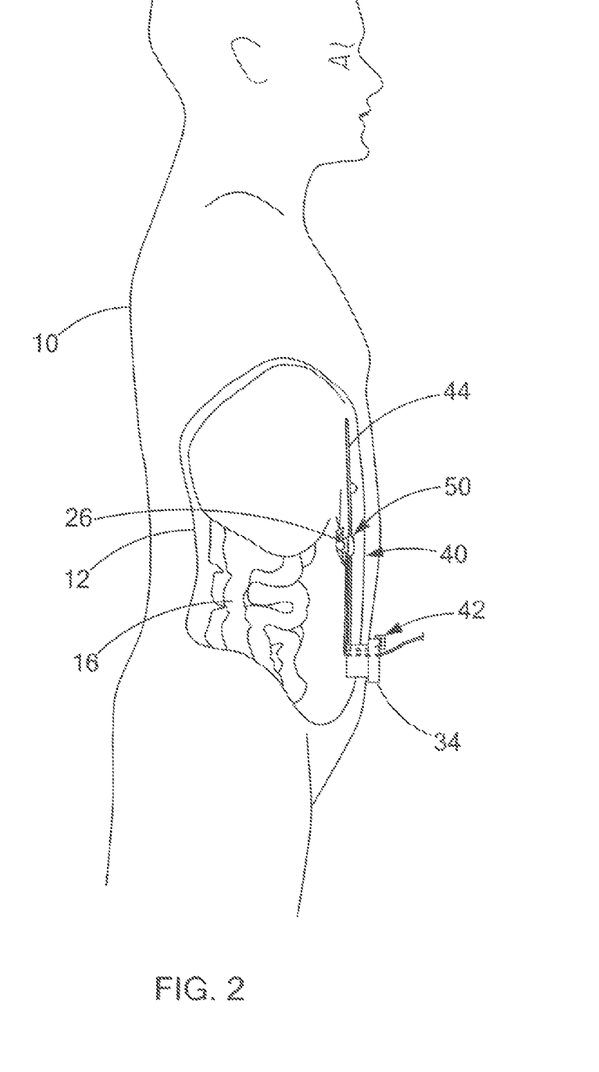
FIG. 2 is a schematic side view of the medical system and medical device depicted in FIG. 1.
Figure 3:
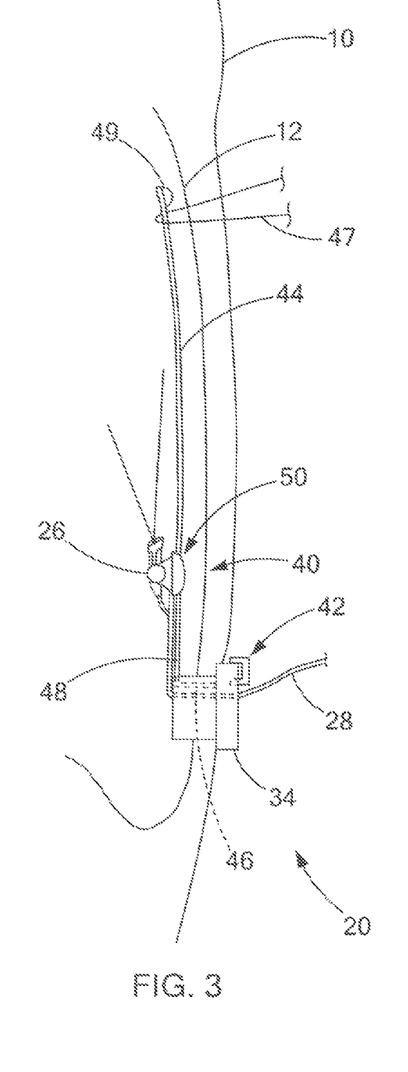
FIG. 3 is an enlarged view of FIG. 2.

Turning now to the Figures, FIGS. 1-3 depict a medical system 20 employing a medical device 40 for performing a laparoscopic procedure on a patient 10. The patient 10 has generally been depicted as a mammalian patient having an abdominal cavity 12 and various organs therein, e.g., the stomach 14 and small intestines 16, etc. It will be readily apparent to those skilled in the art that the medical system 20 and medical device 40 may be employed with many different bodily cavities and bodily structures, and is not limited to those depicted herein.

In addition to the medical device 40, the medical system 20 generally includes one or more medical instruments. As depicted in FIGS. 1-3, one medical instrument includes a camera 26 that generally utilizes a cable 28 or other signal carriers, fiber optics, or wires to transmit video to the physician. It will be recognized that many medical instruments may be deployed via the medical device 40, including catheters, scopes, visualization devices (e.g. lighting), location or orientating devices, insufflation or vacuum devices and the like. The medical system 20 also includes a port 22 that is attached to the patient 10 at a puncture site using methods known to those skilled in the art. A simplified port 22 has been depicted in the figures, and is generally tubular in nature to define a port opening 24 through which the medical device 40 and various medical instruments may pass. The camera 26 is operatively connected to the medical device 40 for use though the port 22. Generally, the medical device 40 serves as a guidance system for directing the camera 26 (or other selected medical device) within the abdominal cavity 12, while still permitting use of additional medical devices through the port 22. By way of example, a laparoscopic grasper and a cutting instrument 32 have been shown in FIG. 1 deployed through the port 22 in conjunction with the camera 26 and medical device 40.

As best seen in FIGS. 2 and 3, the port 22 generally includes a peripheral rim 34 which is at least partially located on the exterior of the patient 10, and to which the medical device 40 is attached. The medical device 40 includes a connection member 42 and a rail 44 attached to the connection member 42 and projecting therefrom. The rail 44 includes a first portion 46 extending through the port opening 24 and second portion 48 which is angled relative to the first portion 46 and projects into the abdominal cavity 12. A carrier 50 is structured to selectively attach to the rail 44 and slide there along. As shown in the Figures, the camera 26 is selectively attached to the carrier 50, whereby it can be guided along the rail 44 of the medical device 40.

Figure 4:
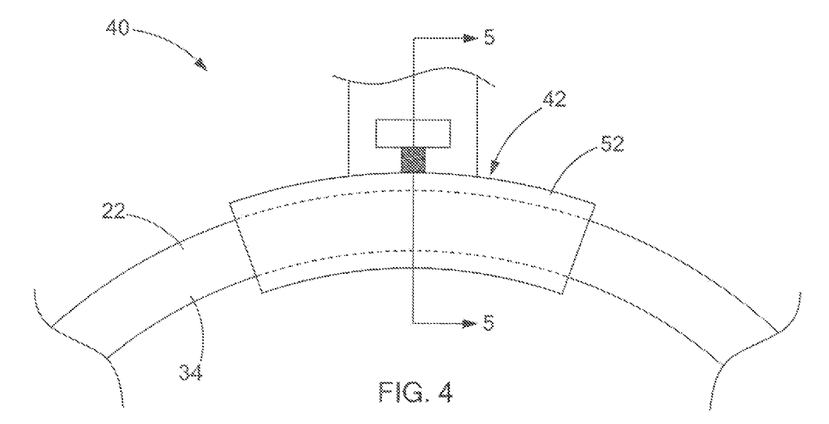
FIG. 4 is an enlarged plan view of a portion of the medical device depicted in FIG. 1.
Figure 5:
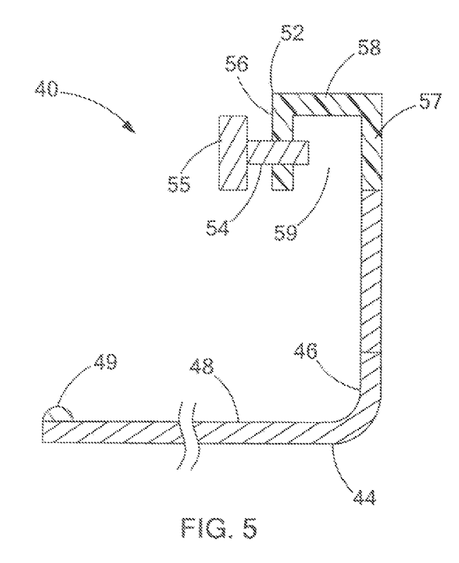
FIG. 5 is a cross-sectional view taken about the line 5-5 in FIG. 4.
Figure 6:
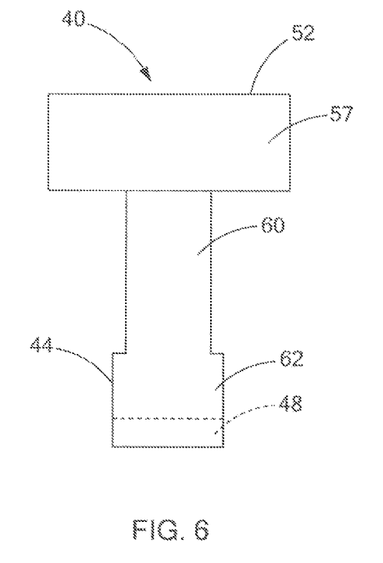
FIG. 6 is a front view of FIG. 4.

One embodiment of the medical device 40 will now be further described with references to FIGS. 4-6. The connection member 42 of the medical device 40 generally includes an open sided channel 52 and a fastener 54. The fastener 54 has been depicted as a threaded fastener having a head or knob 55 which can be turned by hand, although it will be recognized by those skilled in the art that various other fasteners, latches or locks may be utilized to attach the channel 52 and/or rail 44 to the port 22, including friction fits, tabs and detents, clamps and the like. The channel 52 generally includes opposing side walls 56, 57 which are connected by an upper wall 58. The fastener 54 is threaded through the outer side wall 56 through a corresponding hole formed in the wall 56. The side walls 56, 57 are spaced apart to define an interior space 59 that is sized to receive the peripheral rim 34 of the port 22. The fastener 54 projects into the interior space 59 to engage the rim 34 and fix the medical device 40 to the port 22. The fastener 54 may be adjusted via its knob 55 to readily attach and detach the medical device 40, or similarly allow the medical device 40 to be slid around the periphery of the rim 34 for positioning of the medical device 40, and in particular its rail 44. As best seen in FIG. 4, the channel 52 preferably has an arcuate shape sized and structured to match the arcuate shape of the port 22 and its upper rim 34. It will be recognized by those skilled in the art that the channel 52 may have other configurations and structures, e.g. a straight channel or a profiled cross-section, depending on the shape and configuration of the particular port 22.

As best seen in FIGS. 5 and 6, the first portion 46 of the rail 44 generally projects downwardly on the page, and preferably generally parallel to the side wall of the port 22, or generally parallel to an axis of the port opening 24. Notably, the first rail portion 46 takes up minimal space within the port opening 24 and preferably extends along the outer periphery of the opening 24 and alongside the side wall of the port 22. The second rail portion 48 is angled relative to the first portion 46, and as shown in the figures is generally perpendicular thereto. The second rail portion 48 is preferably angled about 45 degrees to about 115 degrees relative to the first rail portion 46. In the present embodiment, the second rail portion 48 is shown as a generally a straight linear member, although it may have some curvature. Preferably, the rail 44 is formed of a relatively rigid material such as a metal, alloy or rigid plastic. The second rail portion 48 is significantly longer than the first rail portion 46, and preferably it is two times to twenty times longer. The rail 44 may be curved in the vertical direction (up and down on the page in FIGS. 5 and 6), or in a horizontal direction (left and right on the page in FIGS. 4 and 6), or both depending on the cavity being explored.

Referring back to FIGS. 2 and 3, it may be desirable for the second rail portion 48 to have some limited flexibility so that it may adapt to the contour of the body cavity 12 and/or other bodily parts. When using the abdominal cavity 12, the rail 44 preferably is sized so that the first rail portion 46 extends slightly beyond the distal end of the port 22, while the second rail portion 48 projects laterally alongside the abdominal tissue layers. It will be recognized by those skilled in the art that depending upon the particular bodily cavity and patient anatomy, the rail 44 may have various sizes. In one preferred embodiment, the rail 44 is constructed of a hard plastic and has a thickness in the range of 0.1 to 1.0 mm, and the first rail portion 46 has a length in the range of 1 mm to 10 mm, and the second rail portion 48 has a length in the range of about 5 mm to about 50 mm. Depending on the length, thickness, material and shape of the second rail portion 48, additional measures may be used to control the proximity of the rail to the abdominal tissue layers. For example, a needle may be used to percutaneously place a suture around the distal end of the second rail portion 48 (or connect a suturing device, wire or the like to the distal end), and the suture can be selectively tensioned to control the position of the distal end. Counter pressure/force can also be placed on the port 22 to help control the inclination of the rail 44, e.g. a downward force can be place on a side of the port 22 that is opposite the direction the second rail portion 48 projects, or a support/wedge may be placed on the other side of the port 22. The counter pressure can be created by the medical professional, weights, shims/wedges, tensioned strings/wires, and other well known structures and apparatus.

Figure 7:
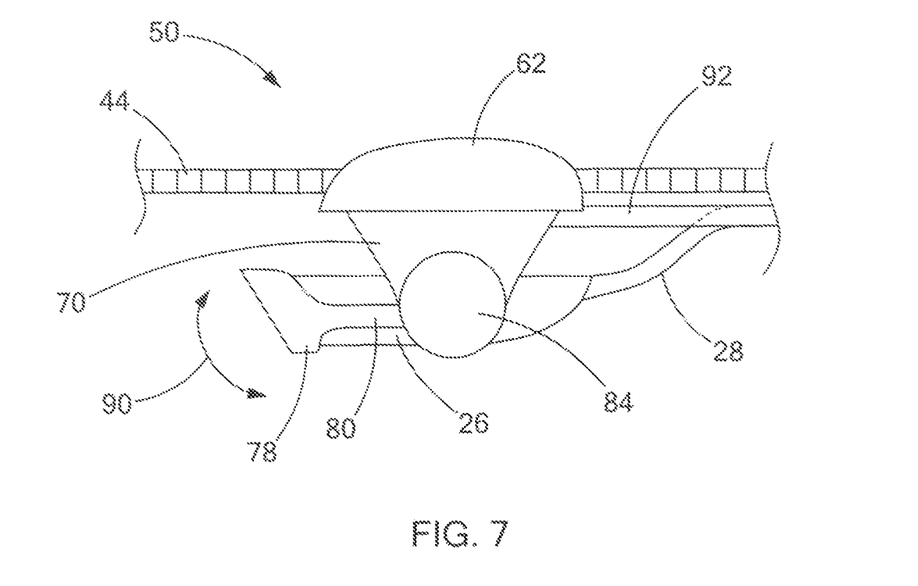
FIG. 7 is a side view of a portion of the medical device depicted in FIG. 1.
Figure 8:
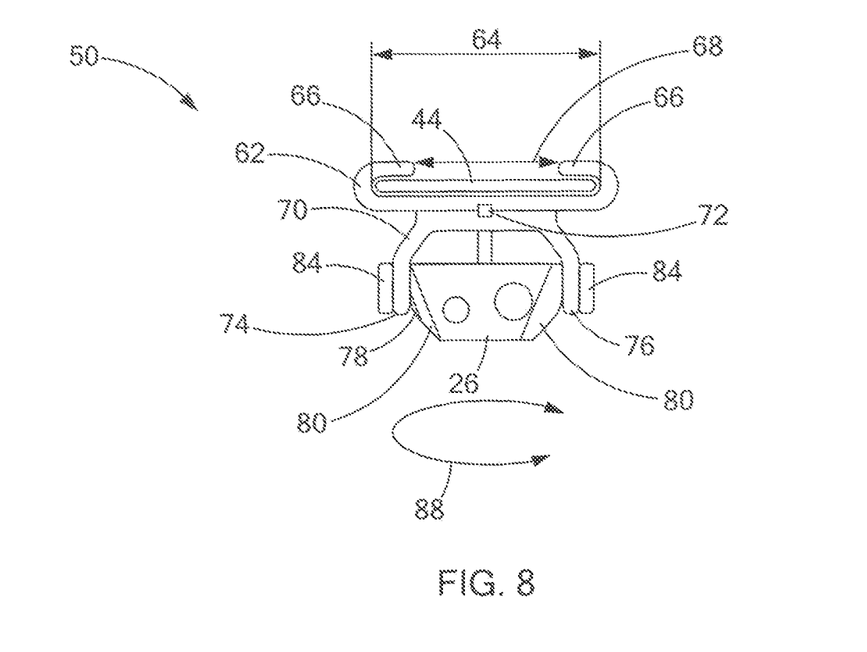
FIG. 8 is a front view of FIG. 7.

As best seen in FIG. 6 the first rail portion 46 preferably includes a reduced diameter 60 or a reduced width portion 60 which allows for selective attachment of the carrier 50 through the rail 44. As best seen in FIGS. 7 and 8, the depicted embodiment of the carrier 50 includes an open sided channel 62 defining an interior space 64 sized to slidably receive the rail 44. The open sided-channel includes lips 66 which define an entrance 68 to the interior space. The entrance 68 generally has a width that is less than the width of the interior space 64, but greater than a width of the reduced width section 60 or the first rail portion 46. Accordingly, it will be recognized that the open sided-channel 62 of the carrier 50 may be selectively attached and detached from the rail 44 at the reduced width portion 60 of the rail 44. The second rail portion 48 and the carrier 50 are structured such that the carrier 50 cannot detach therefrom, and the second rail portion 48 may further include a stop 49 at its distal end in relation to this purpose.

When attached to the rail, the carrier 50 may be slid therealong. Accordingly, the transition from the first rail portion 46 to the second rail portion 48 is generally radiused so that the carrier 50 may easily transition therebetween. The interior space 64 may be sized larger than the rail 44 to leave a gap therebetween to allow for some play as the carrier 50 is slid along the rail 44. The carrier 50 preferably also includes a flange 70 that is rotatably attached to the open side-channel 62 via a pivot pin 72. The flange 70 includes opposing arms 74, 76 which are sized to receive the camera 26 therebetween. A bracket 78 is rotatably attached to the flange 70, and in particular the bracket includes two bracket arms 80, 82 which are sized to engage the camera 26. Each of the bracket arms 80, 82 are rotatably attached to the opposing arms 74, 76 respectively, via pivot pins 84, 86.

Accordingly, it will be seen that the open sided-channel 62 can slide proximal and distally along the rail 44, while the camera 26 may rotate in two dimensions relative to the channel 62 and rail 44. The bracket 70 may rotate about a vertical axis (up and down on the page in FIGS. 7 and 8) via pivot pin 72, and as indicated by arrow 88 (FIG. 8), while the bracket 78 may rotate up and down about pivot pins 84 (i.e. about a horizontal axis extending left to right on a page in FIG. 8) as indicated by the arrow 90 (FIG. 7). A control wire 92 is preferably attached to any one of the components of the carrier 50, e.g. any of the bracket 78, flange 70 or channel 62. Similarly, the camera 26 includes the cable 28 which can also be used to translate the camera 26 along the rail 44, as well as affect rotation of the camera 26 via pivoting of the components of the carrier 50. Accordingly, it will be recognized that the control wire 92 and the transmission member 28 may be used alone or in combination to manipulate the camera 26, and may be coupled together or incorporated into a common bundle. Likewise, small motors, prime movers or effectors may be incorporated into the carrier 50 so that pivoting of the various components and rotation of the camera 26 may be effectuated electronically and remotely via either of the rail, the control member 92 and the transmission member 28.

Figure 9:
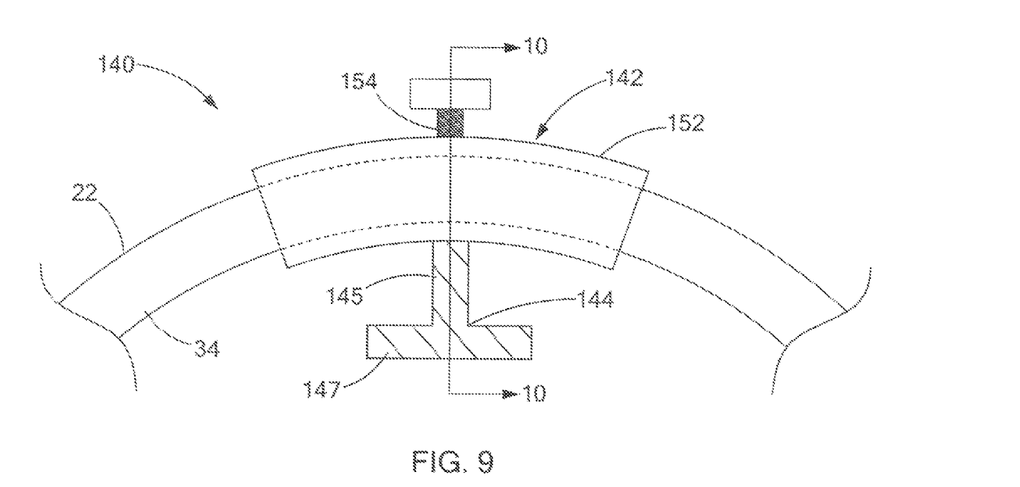
FIG. 9 is an enlarged plan view of another embodiment of a medical device constructed in accordance with the teachings of the present invention.
Figure 10:
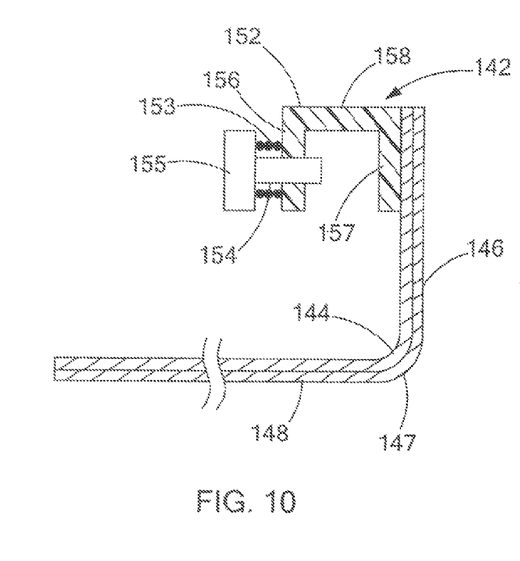
FIG. 10 is a cross-sectional view taken about the line 10-10 in FIG. 9.
Figure 11:
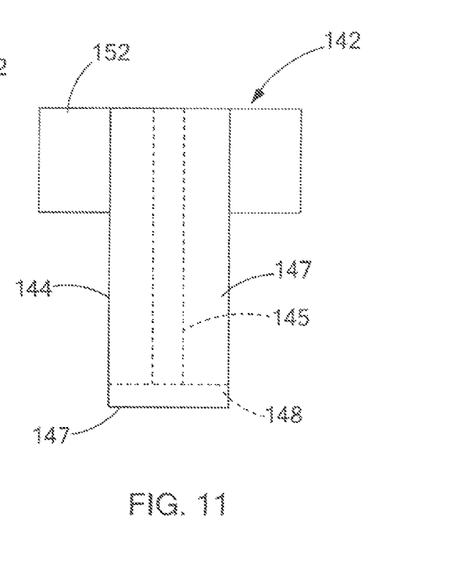
FIG. 11 is a front view of the medical device depicted in FIG. 9.

It will be recognized by those skilled in the art that many variations of the medical device 40, and in particular the connection member and rail, are possible depending upon the type of procedure being formed, the type of patient, and the intended use of the medical system 20 and device 40. One variation is shown in the embodiment of FIGS. 9-11, which depicts the medical device 140 again having a connection member 142 and a rail 144. In this embodiment, the connection member 42 again includes an open sided-channel 152 structured for connection to the peripheral rim 34 of the port 22. Here the fastener 154 is not a threaded fastener, but rather is a pin and a compression spring 153 extending between the knob 155 and the outer side wall 156 of the channel 52. The spring 153 urges the fastening pin 154 into engagement with the peripheral rim 34 of the port 22.

In the embodiment of FIGS. 9-11, it will also be recognized that the rail 144 has been formed with a T-shaped cross-section. In particular, the rail has a cross-section including a radial portion 145 and a lateral portion 147 connected to the radial portion 145. The radial portion 145 is connected to the inner side wall 157 of the channel 152. As best seen in FIG. 10, the rail 144 again includes a first portion 146 projecting downwardly and generally parallel to the wall and axis of the port 22, and then transitions to a second portion 148 which is angled relative to the first portion 146. As in the previous embodiment, the transition area 147 from the first rail portion 146 to the second rail portion 148 is radiused to provide smooth sliding of the carrier along the rail 144.

Figure 12:
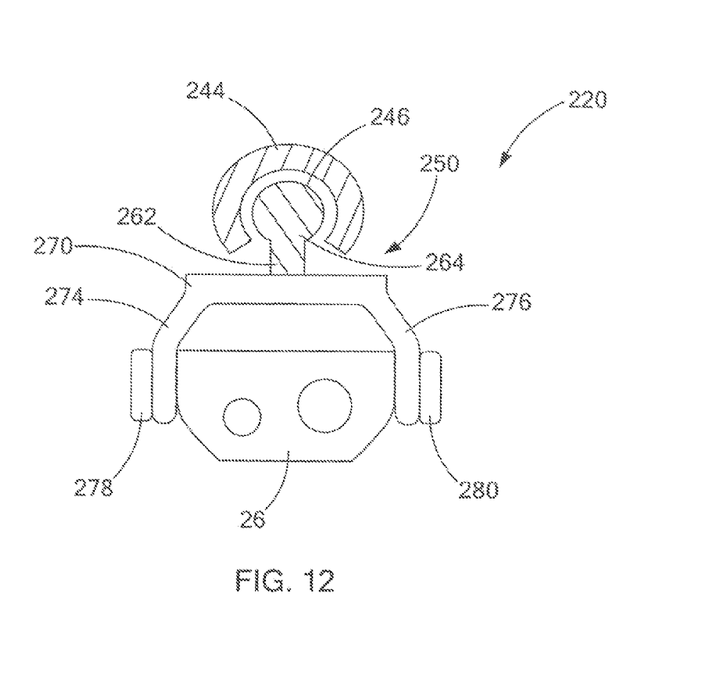
FIG. 12 is a front view similar to FIG. 8, but showing an alternate embodiment of a portion of the medical device depicted in FIG. 1.
Figure 13:
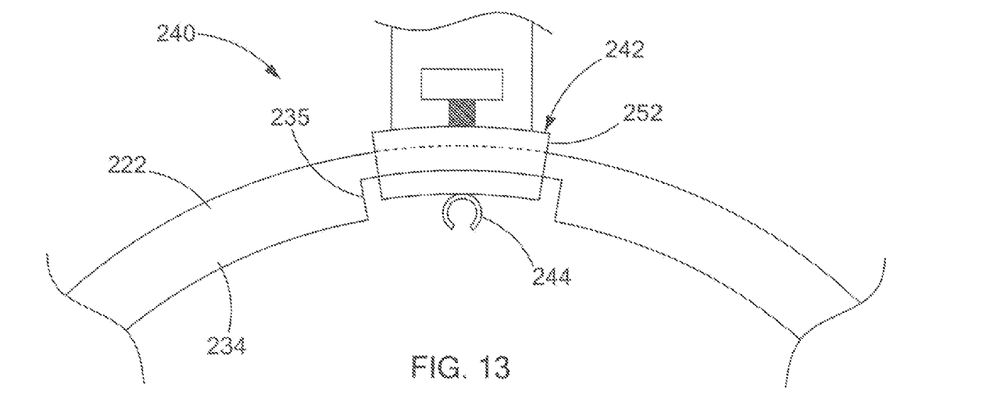
FIG. 13 is an enlarged plan view of another embodiment of a medical device constructed in accordance with the teachings of the present invention.

Yet another embodiment of a medical system 230 has been depicted in FIGS. 12-13, constructed in accordance with the teachings of the present invention. In this embodiment, the rail 244 has been depicted as having a curved or semi-annular shape to define an interior space 246 sized to receive the carrier 250. Instead of the open sided-channel 62 which wrapped around the rail 44 in previous embodiments, here the carrier 250 includes its own rail 262 having a semi-spherical head 264. The semi-spherical head 264 is sized to slidably and rotatably be received within the interior space 246 of the rail 244. The carrier 250 includes a flange 270 having opposing flange arms 274, 276 which are sized to engage the camera 26. Preferably, the camera 26 is rotatably attached to the flange arms 274, 276 by corresponding pivots 278 and 280. It will be recognized that in this embodiment, rather than the carrier including a member which receives the rail, here the rail is structured to receive a portion of the carrier. These and many other variations on the embodiments of the medical systems and devices depicted herein will be readily apparent to those skilled in the art. It can also be seen in FIG. 13 that the port 222, including its rim 234, has been formed with a reduced thickness portion that defines a pocket 235. The pocket 235 may be sized to completely or partially receive the rail 244. The connection member 242 and its channel 252 are sized to engage the rim 234 within the pocket 235, and the rail 244 is attached to the channel 252. In this manner, the size of the port opening 224 is maximized for other medical instruments or devices.

Figure 14:
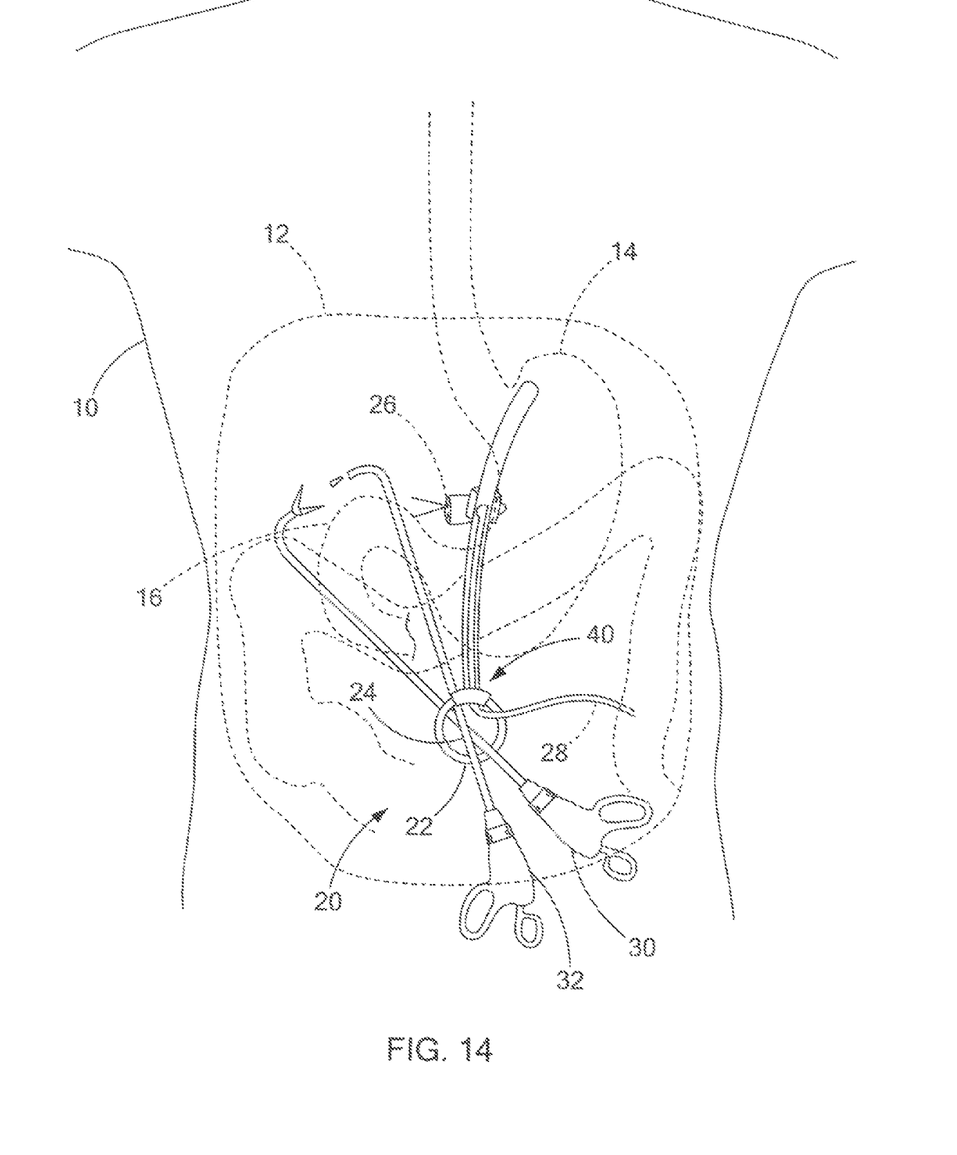
FIG. 14 is a schematic plan view of an alternate embodiment of a medical system and device constructed in accordance with the teachings of the present invention.

Yet another alternate embodiment of the medical system and device have been depicted in FIG. 14. The medical system and device depicted therein are substantially similar to the prior embodiments, but depicts that the rail 344, and in particular the second portion of the rail 348 not only bend slightly under its own weight, but may also be formed with a curvature to assist in accessing particular bodily cavities or structures within the patient 10. Accordingly, it will be recognized that the rail portion of the medical device and system may have many different sizes, shapes and configurations depending upon the particular procedure, patient and application.

A method of employing the medical system 20 and medical device 40 to access a bodily cavity, e.g. to diagnose a condition or to perform a medical procedure within the bodily cavity, will now be described. A port 22 is attached to a bodily wall proximate the bodily cavity to maintain an opening formed through the skin and related tissue layers of the patient. The rail 44 of the device 40 is passed distally through the port opening 24 and into the bodily cavity. The rail 44 is preferably angled as it passes through the port opening 24 so that it can be slid along the tissue defining the cavity. The connection member is attached to the port, for example using the latch 54 discussed above. The carrier 50 is connected to the rail, and a medical instrument (e.g. the camera 26) is connected to the carrier 50. The medical instrument 26 and carrier 50 are slid along the rail 44 and into the bodily cavity. Additional instruments may then be employed through the port opening 24 as shown in FIG. 1. When the physician has completed using the medical instruments, the carrier 50 and camera 26 are slid proximally along the rail. The camera 26 or other medical instrument may then be detached from the carrier 50. Alternatively, the carrier 50 may be slid proximally and a second medical instrument may replace the camera 26 on the carrier 50. It will also be recognized that the carrier 50 may be adapted to connect to multiple instruments simultaneously as well as alternately.

Accordingly, it will be recognized by those skilled in the art that medical devices and systems of the present invention can serve as a guidance system for directing one or more selected medical devices within a bodily cavity, while still permitting use of additional medical devices through the port. As such, only one laparoscopic port is needed, thereby minimizing scars and potential complications from perforations and punctures through the skin and related tissue layers.

It will also be recognized by those skilled in the art that, while the methods described above generally include passing through tissue and into an internal bodily cavity or lumen, it will be recognized that the systems, devices and methods may be used on any layer of material (e.g. fabrics, cloth, polymers, elastomers, plastics and rubber) that may or may not be associated with a human or animal body and a bodily lumen. For example, the systems, devices and methods can find use in laboratory and industrial settings for placing devices through one or more layers of material that may or may not find application to the human or animal body, and likewise closing holes or perforations in layers of material that are not bodily tissue. Some examples include viewing behind structures such as walls, plates, floors, rubble (e.g. in rescue work), as well as working with synthetic tissues, polymeric sheets, animal studies, veterinary applications, and post-mortem activities.

The foregoing description of various embodiments of the invention has been presented for purposes of illustration and description. It is not intended to be exhaustive or to limit the invention to the precise embodiments disclosed. Numerous modifications or variations are possible in light of the above teachings.

The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical device for accessing a bodily cavity through a port, the port structured for attachment to a bodily wall and defining a port opening, the medical device comprising:
   a connection member for fixing the position of the medical device relative to the port;
   a rail attached to the connection member, the rail having a first portion being attached to the connection member and configured to extend distally through the port opening, and a second portion extending at an angle relative to the first portion, the angle being permanently fixed, the second portion having a length, the first portion being proximal to the second portion when connected to the port; and
   a carrier structured to selectively connect to the first portion of the rail, the carrier slidable along the first and second portions of the rail, the carrier being shorter than the length of the second portion.

2. The medical device of claim 1, wherein the rail is structured such that the carrier can slide distally along the rail from the first portion to the second portion, and wherein the carrier and second portion of the rail are structured such that the carrier cannot be disconnected from the second portion of the rail.

3. The medical device of claim 1, wherein the carrier includes an open-sided channel sized to slidably receive the rail.

4. The medical device of claim 1, wherein the carrier includes a linking member, and wherein the rail includes an open sided-channel sized to slidably receive the linking member of the carrier.

5. A medical device for accessing a bodily cavity through a port, the port structured for attachment to a bodily wall and defining a port opening, the medical device comprising:
   a connection member for fixing the position of the medical device relative to the port;
   a rail attached to the connection member, the rail having a first portion being attached to the connection member and configured to extend distally through the port opening, and a second portion extending at an angle relative to the first portion, the second portion having a length, the first portion being proximal to the second portion when connected to the port; and
   a carrier structured to selectively connect to the first portion of the rail, the carrier slidable along the first and second portions of the rail, the carrier being shorter than the length of the second portion, wherein the rail is formed of a bar having a width, and wherein the first portion has a reduced width section structured to permit the carrier to selectively connect to the rail.

6. The medical device of claim 1, wherein the second portion is longer than the first portion.

7. The medical device of claim 1, wherein the rail is elongated, and wherein the second portion is curved as it extends longitudinally.

8. The medical device of claim 1, wherein the second portion extends perpendicularly to the first portion.

9. The medical device of claim 1, wherein the second portion is angled relative to the first portion in the range of 45 degrees to 115 degrees.

10. The medical device of claim 1, wherein the first portion has a length in the range of 1 mm to 10 mm, and the second portion has a length in the range of 5 mm to 50 mm.

11. A medical system comprising the medical device of claim 1 and further comprising:
   a port defining a port opening, the port structured for attachment to a bodily wall proximate the bodily cavity; and
   an elongate pusher member having a distal end connected to the carrier.

12. The medical system of claim 11, wherein the port includes an annular side wall extending around a port axis, and wherein a portion of the annular side wall is spaced further away from the port axis than an adjacent portion of the annular side wall to define a pocket, and wherein the rail is positioned substantially within the pocket.

13. The medical system of claim 11, wherein the carrier includes an instrument connector and the system includes a medical instrument connected to the instrument connector, and wherein the pusher member includes a control wire connected to one of the instrument connector and the medical instrument.

14. The medical system of claim 11, wherein the connection member includes a hook-shaped body structured to extend around a proximal rim of the port.

15. A medical system for accessing a bodily cavity through a bodily wall comprising:
   a port defining a port opening, the port structured for attachment to the bodily wall proximate the bodily cavity;
   a connection member structured for attachment to the port, wherein the connection member includes a latch structured to selectively fix the position of the connection member on the port;
   a rail attached to the connection member, the rail having a first portion extending distally through the port opening, and a second portion extending at an angle relative to the first portion;
   a carrier structured to selectively connect to the first portion of the rail, the carrier slidable along the first and second portions of the rail; and
   an elongate pusher member having a distal end connected to the carrier.

16. The medical device of claim 1, wherein the carrier is slidable along the first portion of the rail, the angle between the first and second portion of the rail, and the second portion of the rail, the angle being greater than 0 degrees.

17. The medical device of claim 1, wherein the carrier slides along the first portion of the rail in a first direction, and slides along the second portion of the rail in a second direction, the first direction angled relative to the second direction.

18. The medical device of claim 1, wherein the carrier travels through the angle between the first portion and second portion of the rail such that the carrier travels in two different directions that are not parallel.

19. The medical system of claim 15, wherein the latch is separate from the carrier member.

20. A medical system for accessing a bodily cavity through a bodily wall comprising:
   a port defining a port opening, the port structured for attachment to the bodily wall proximate the bodily cavity;
   a connection member structured for attachment to the port, the connection member including a hook-shaped body structured to extend around a proximal rim of the port;
   a rail attached to the connection member, the rail having a first portion extending distally through the port opening, and a second portion extending at an angle relative to the first portion;
   a carrier structured to selectively connect to the first portion of the rail, the carrier slidable along the first and second portions of the rail; and
   an elongate pusher member having a distal end connected to the carrier.

21. The medical device of claim 15, wherein the angle between the first and second portions is permanently fixed.

22. The medical device of claim 15, wherein the angle between the first and second portions remains fixed when the carrier is slid along the second portion.

23. The medical device of claim 15, wherein the second portion of the rail has a length, and wherein the carrier is shorter than the length of the second portion of the rail.

24. The medical device of claim 15, wherein the second portion is longer than the first portion.

* * * * *